(12) United States Patent
Biagini et al.

(10) Patent No.: US 8,188,304 B2
(45) Date of Patent: May 29, 2012

(54) PROCESS FOR THE PURIFICATION OF LANTHANIDE CARBOXYLATES

(75) Inventors: Paolo Biagini, Trecate (IT); Mario Salvalaggio, Moriondo Torinese (IT); Franco Cambisi, Oleggio (IT); Lucia Bonoldi, Milan (IT); Liliana Gila, Casalino (IL)

(73) Assignee: Polimeri Europa S.p.A., Brindisi (IT)

( * ) Notice: Subject to any disclaimer, the term of this patent is extended or adjusted under 35 U.S.C. 154(b) by 953 days.

(21) Appl. No.: 11/689,719

(22) Filed: Mar. 22, 2007

(65) Prior Publication Data
US 2007/0232794 A1 Oct. 4, 2007

(30) Foreign Application Priority Data
Mar. 31, 2006 (IT) .................................. MI06A0619

(51) Int. Cl.
C07F 13/00 (2006.01)
C07C 63/36 (2006.01)
C07C 53/00 (2006.01)
(52) U.S. Cl. ............................ 554/71; 562/490; 562/606
(58) Field of Classification Search .................. None
See application file for complete search history.

(56) References Cited

U.S. PATENT DOCUMENTS
6,846,432 B2 * 1/2005 Mills ............................ 252/180

FOREIGN PATENT DOCUMENTS
| EP | 0 564 081 A2 | 10/1993 |
| WO | WO 97/36850 | 10/1997 |
| WO | WO 98/39283 | 9/1998 |
| WO | WO 99/54335 | 10/1999 |

OTHER PUBLICATIONS

Armarego et al, Purification of Laboratory Chemicals, 4th Edition, 2000, pp. 1-47.*

* cited by examiner

Primary Examiner — Paul A Zucker
(74) Attorney, Agent, or Firm — Oblon, Spivak, McClelland, Maier & Neustadt, L.L.P.

(57) ABSTRACT

A process is described for the purification of lanthanide carboxylates which comprises a step in which the hydrocarbon solution deriving from the synthesis of lanthanide carboxylate, containing said carboxylate and impurities of the corresponding carboxylic acid and/or water, is treated with an aqueous solution of a base in order to obtain a pH of the aqueous phase ranging from 9.0 to 12.2 and/or a step in which the hydrocarbon solution containing lanthanide carboxylate is treated with a solid selected from $Na_2SO_4$, $MgSO_4$, $Mg(ClO_4)_2$, molecular sieves 3 Å, molecular sieves 4 Å, molecular sieves 5 Å and molecular sieves 13 X. Analytical methods are also described, which allow the purity of the lanthanide carboxylates to be non-destructively measured.

21 Claims, 4 Drawing Sheets

PROCESS FOR THE PURIFICATION OF LANTHANIDE CARBOXYLATES

A process is described for the purification of lanthanide carboxylates which comprises a step in which the hydrocarbon solution deriving from the synthesis of lanthanide carboxylate, containing said carboxylate and impurities of the corresponding carboxylic acid and/or water, is treated with an aqueous solution of a base in order to obtain a suitable pH of the aqueous phase, and/or a step in which the hydrocarbon solution containing lanthanide carboxylate is treated with a solid selected from $Na_2SO_4$, $MgSO_4$, $Mg(ClO_4)_2$, molecular sieves 3 Å, molecular sieves 4 Å, molecular sieves 5 Å and molecular sieves 13 X.

Analytical methods are also described, which allow the purity of the lanthanide carboxylates to be non-destructively measured.

Polybutadiene with a high content of 1,4-cis units (>90%) is produced industrially with the use of catalysts of the Ziegler-Natta type, which consist of compounds of transition metals or of the series of lanthanides in the presence of one or more cocatalysts. Among these catalytic systems, those based on the use of compounds of elements of the series of lanthanides, are particular interesting as they have a wide range of conditions of use, they provide polymers with an extremely high content of 1,4-cis units (>96%) and can operate in solvents completely free of aromatic hydrocarbons.

In the presence of suitable activators, many derivatives of metals of the series of lanthanides can generate valid catalytic systems for the production of 1,4-cis polybutadiene, but among all of these, those which have been most widely used are undoubtedly carboxylates. The reasons lie in the fact that these compounds are generally easy to synthesize starting from easily available and low-cost precursors, furthermore they do not have to be kept in an inert environment and, depending on the carboxylic acid used, they are extremely soluble in aliphatic hydrocarbons, i.e. in the solvents in which the polymerization process of butadiene generally takes place.

Numerous synthesis methods of lanthanide (Ln) carboxylates provide materials, solid or in solution, which contain, in addition to the desired product $Ln(OOCR)_3$, varying quantities of the corresponding carboxylic acid RCOOH and/or $H_2O$. U.S. Pat. No. 5,783,676, for example, describes a method for obtaining solid $Nd(Vers)_3$ by the reaction between $Na(Vers)$ and $Nd(NO_3)_3$ using mixtures of methanol/water as solvent: under these conditions, the products obtained contain up to 5% by weight of free versatic acid and varying quantities of $H_2O$, in any case >0.1% by weight, in relation to the particular experimental conditions adopted. Analogously U.S. Pat. No. 6,054,563 and U.S. Pat. No. 6,090,926 describe a method for obtaining solid $Nd(Vers)_3$ starting from the corresponding hydrocarbon solutions containing $H_2O$ (from 0.005 to 3% by weight) and free versatic acid (from 0.005 to 12% by weight), in some cases a series of solubilizing agents among which the same carboxylic acids, are added to the solutions, before the drying phase.

With respect to the production of hydrocarbon solutions containing neodymium carboxylates, two main strategies are adopted. The first consists in reacting $Nd_2O_3$ directly with the desired carboxylic acid, mainly versatic acid or naphthenic acid, in the presence of catalytic quantities of HCl, and varying quantities of $H_2O$ and/or neodymium salts such as $NdCl_3$ or $Nd(NO_3)_3$ are sometimes added, in order to facilitate the reaction. Valid examples of this synthesis method are described in U.S. Pat. No. 4,710,553, U.S. Pat. No. 5,686,371, EP 0,562,081, EP 0,968,992, U.S. Pat. No. 6,111,082 and U.S. Pat. No. 6,482,906. The amount of $H_2O$ and carboxylic acid present in the final solutions are not always mentioned in the examples considered, but the available data suggest that, under these conditions, the molar ratios $H_2O/Nd$ and carboxylic acid/Nd in the final hydrocarbon solutions can vary from 0.2 to values higher than 1.5. In some case, such as in EP 0.968.992 and U.S. Pat. No. 6,111,082, the quantity of $H_2O$ is considerably reduced through an azeotropic distillation, but in no case are described operations which intend to eliminate or reduce the amount of free carboxylic acid present in the $Nd(Ver)_3$ solutions.

A second strategy envisages a reaction between neodymium salts, such as, for example, $NdCl_3$ or $Nd(NO_3)_3$, with sodium carboxylates or carboxylic acids in the presence of amines, in water as solvent. In this way, the corresponding neodymium carboxylate is formed and can be subsequently extracted by means of organic solvents as described in U.S. Pat. No. 4,520,177 and U.S. Pat. No. 4,689,368, or the product is obtained directly in an organic solution, if the reaction is effected in the presence of an $H_2O$/organic solvent double phase as exemplified in U.S. Pat. No. 5,220,045, U.S. Pat. No. 6,111,082 and WO 02/076992. This synthesis method also produces solutions of $Nd(Vers)_3$ containing variable amounts of free carboxylic acid and water. The quantity of the latter is, in many cases, decreased through azeotropic distillations, but nothing is done to decrease the amount of free acid present in the solutions. On the contrary, as declared in U.S. Pat. No. 6,111,082 and WO 02/076992, it is necessary to add further amounts of solubilizing agents, among which also the same carboxylic acids, to allow the hexane solutions of $Nd(Vers)_3$, obtained with this method, to remain stable for long periods of time.

The free carboxylic acid present in the solutions or in the solid products based on $Nd(Vers)_3$, can derive from the use of an excess of this reagent in the attack reaction of the corresponding oxide, whereas water can be present both because it is used as solvent, for example in reactions between salts of lanthanides and sodium carboxylates, and also because it is produced in the reactions between lanthanide oxides ($Ln_2O_3$) and carboxylic acids. In some cases, as mentioned above, the addition of variable quantities of carboxylic acid is described with the purpose of improving the stability of the hydrocarbon solutions of lanthanide carboxylates.

The presence of variable and non-reproducible amounts of carboxylic acid and/or water in the solutions containing lanthanide carboxylates can cause considerable drawbacks during the activation phase, before polymerization, which normally includes the use of alkylating agents, such as, for example, aluminum alkyls. As it is known to experts in the field, the presence of substances containing acidic hydrogens, as in the case of carboxylic acids and water, causes an immediate hydrogenolysis reaction of the alkylating reagent with the formation of the corresponding carboxylates or oxides. From this it follows that, in the formulation of the catalytic system, a higher quantity of alkylating reagent must be used and, as these products normally have a high cost with respect to the other components, this operation considerably increases the relative costs of the catalytic system.

Furthermore, when derivatives based on aluminum are used as alkylating agents, the relative products of partial hydrogenolysis which are obtained by reaction with carboxylic acids and water, consist of dialkyl aluminum carboxylates and alumoxanes, respectively; these products are normally soluble in hydrocarbon solvents and therefore can react with the catalytic system and modify its characteristics, both by causing a decrease in the polymerization kinetics and by modifying the profile of the molecular weight distribution of the polybutadiene produced.

It is therefore evident that it would be desirable to avail of a method which allows the production of solutions of carboxylates of lanthanides with no carboxylic acid or water at all, or the lowest possible amount thereof, in order to optimize the aluminum consumption and maintain constant the characteristics of the polybutadiene produced, and it would also be useful to have a simple, rapid and non-destructive analytical method and easy to use, in order to directly determine the residual amount of carboxylic acid and water, or possibly the sum of the two products, in these solutions.

A method has now been found by the Applicant, for regulating the quantity of carboxylic acid and water present in hydrocarbon solutions of lanthanide carboxylate, until complete elimination.

Figure 1:
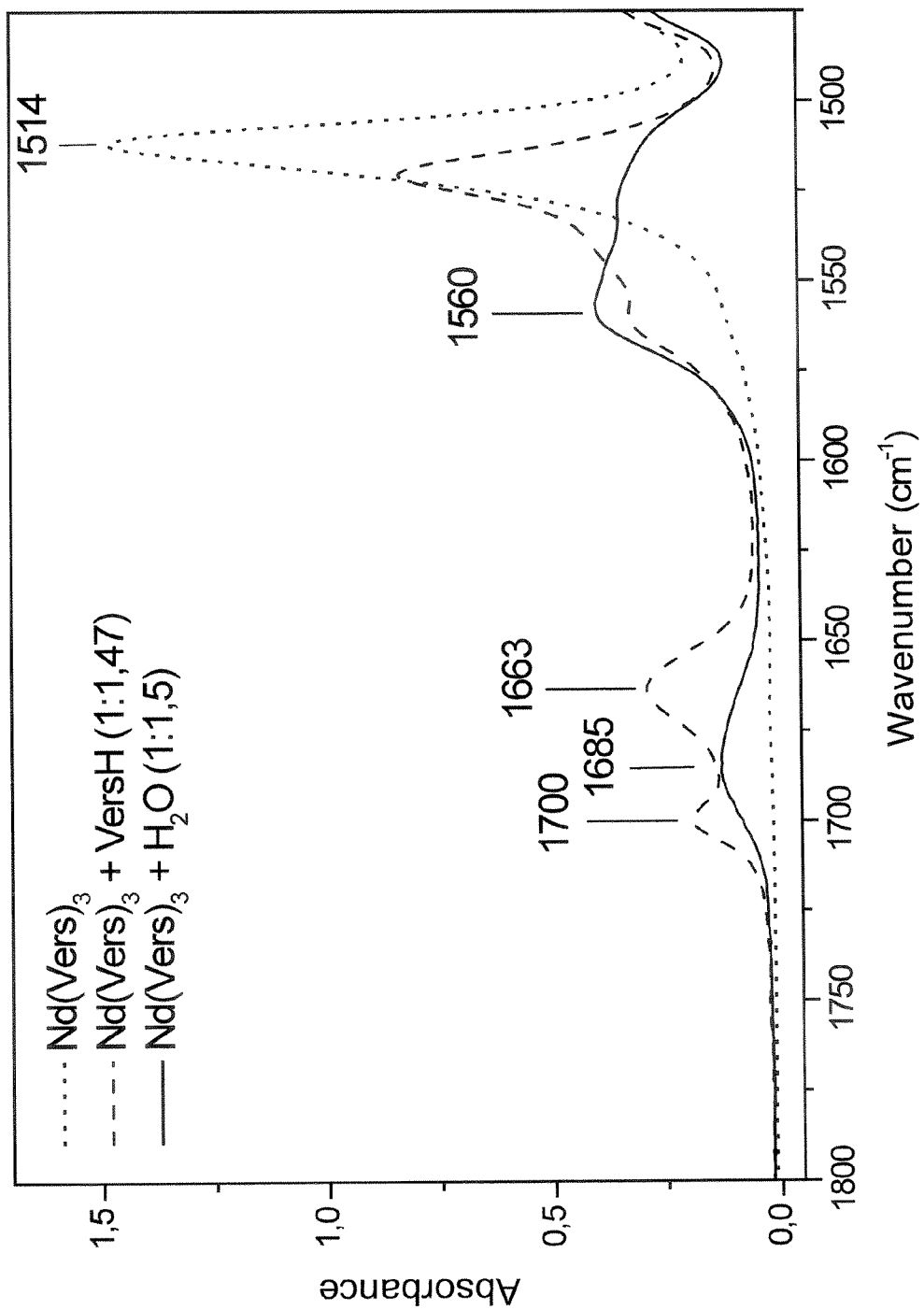
FIG. 1. The IR spectrum of a cyclohexanic solution of pure $Nd(Vers)_3$ (dotted line) and the IR spectrum obtained after the addition, to the same solution, of versatic acid (broken line, $Nd(Vers)_3$/VersH molar ratio 1:1.47).

An object of the present invention therefore relates to a method for the purification of a hydrocarbon solution deriving from the synthesis of a lanthanide carboxylate, containing said carboxylate and impurities of the corresponding carboxylic acid and/or water, which comprises at least one of the following steps:
a) treating the hydrocarbon solution, containing the lanthanide carboxylate, with an aqueous solution of a base so as to obtain a pH of the aqueous phase ranging from 9.0 to 12.2;
b) treating the hydrocarbon solution containing the lanthanide carboxylate with a solid selected from $Na_2SO_4$, $MgSO_4$, $Mg(ClO_4)_2$, molecular sieves 3 Å, molecular sieves 4 Å, molecular sieves 5 Å and molecular sieves 13 X.

If the solution containing the carboxylate is subjected to both forms of treatment, the treatment of step (a) is first carried out and the resulting solution is then subjected to the treatment of step (b).

In step (a) the base solution is added to the hydrocarbon solution until the pH value of the aqueous phase remains stably within the range claimed. The pH of the aqueous phase is preferably included within the range of 10.5-12.0, even more preferably between 11.0 and 11.8. The aqueous solution used, containing the base, preferably has a concentration ranging from 0.01 to 2 M. At the end of the treatment of step (a), the organic phase is separated from the aqueous phase.

The selection, in step (a), of the particular pH range claimed, allows the purification of a hydrocarbon solution containing a lanthanide carboxylate by means of salification and removal from said organic phase of the carboxylic acid in excess or possibly non-reacted, at the end of the synthesis of the lanthanide carboxylate which uses this acid as starting reagent. It is completely unexpected that by putting the hydrocarbon solutions containing a lanthanide carboxylate in contact with a strongly basic aqueous phase, in accordance with the process of the present invention, the stability of said solutions is not influenced, as insoluble products are not formed and there is also no formation of mixed products, in which a fraction of the carboxylate ligands, initially present on the lanthanide, is substituted by oxide or hydroxide groups.

The following bases can be used in step (a) of the present invention: hydroxides and oxides of alkaline and alkaline-earth metals, ammonia and organic amines such as, for example, methyl amine, dimethyl amine, trimethyl amine, ethyl amine, propyl amine, butyl amine, pyridine. According to a preferred aspect sodium hydroxide or potassium hydroxide are used, even more preferably sodium hydroxide.

The hydrocarbon solution is preferably a cyclohexanic solution.

The carboxylic acids which can be removed, by means of the process of the present invention, from the solutions of the corresponding lanthanide carboxylate, can be C2-C40 acids, selected from aliphatic, cyclo-aliphatic, alicyclic and aromatic, mono- and polycarboxylic, preferably C6-C20, even more preferably C8-C12. Typical examples of acids which can be treated with the process of the present invention, are acetic acid, propionic acid, butyric acid, isobutyric acid, pivalic acid, 2-methyl butanoic acid, 3-methyl butanoic acid, cyclohexane carboxylic acid, 1,4-cyclohexane dicarboxylic acid, 1,2-cyclohexane dicarboxylic acid, benzoic acid, cyclohexyl acetic acid, phenyl acetic acid, 3,5-dimethyl hexanoic acid, 2-ethyl hexanoic acid, 3-ethyl hexanoic acid, octanoic acid, iso-octanoic acid, versatic acid (blend of carboxylic acids which can be found on the market with a predominant C10 fraction and with an acid number generally ranging from 310 to 325 mg KOH/g), naphthenic acids (blend of carboxylic acids which can be found on the market with an acid number generally ranging from 160 to 300 g KOH/g), lauric acid, palmitic acid, stearic acid, oleic acid, linoleic acid.

The acids are preferably: versatic acid, naphthenic acid and 2-ethyl hexanoic acid. Impurities of other carboxylic acids possibly present in solution, such as, for example, acetic acid, propionic acid, butyric acid, stearic acid, present individually or in a mixture thereof, in solutions of, for example, neodymium versatate, neodymium naphthenate or neodymium 2-ethyl hexanoate, are also efficaciously removed from the hydrocarbon solution by means of the process of the present invention.

The lanthanide carboxylate solutions which can be treated with the method of the present invention can be, for example, solutions of neodymium, praseodymium, gadolinium, lanthanum carboxylates and any mixture thereof. In particular the hydrocarbon solutions containing neodymium versatate, neodymium naphthenate, neodymium 2-ethyl-hexanoate can be suitably treated with the process of the present invention.

Step b) allows the purification of the hydrocarbon solution of lanthanide carboxylate by removing the water contained in said solutions. The hydrocarbon solution is preferably a cyclohexanic solution. The solid materials used in step b) are added directly to said hydrocarbon solution: their complete insolubility under these conditions and the fact that their reaction with $H_2O$ does not generate other products, guarantee that there is no pollution of the lanthanide carboxylate solutions.

Surprisingly, the treatment of step b) does not cause precipitation or physical or chemical adsorption of the metal on the solid surface, the whole quantity of lanthanide carboxylate which is present, remains in solution.

The molecular sieves 3 Å are characterized by the formula $K_nNa_{12-n}[(AlO_2)_{12}(SiO_2)_{12}]$, the molecular sieves 4 Å by the formula $Na_{12}[(AlO_2)_{12}(SiO_2)_{12}]$, the molecular sieves 5 Å by the formula $Ca_nNa_{12-2n}[(AlO_2)_{12}(SiO_2)_{12}]$ and the molecular sieves 13X by the formula $Na_{86}[(AlO_2)_{86}(SiO_2)_{106}]$. According to a preferred aspect of the present invention, molecular sieves 3 Å, molecular sieves 4 Å or a mixture thereof are used, even more preferably molecular sieves 3 Å are adopted.

The quantity of $H_2O$ expressed as moles/liter, initially present in the lanthanide carboxylate solutions depends on the synthesis method used and, as water chemically binds with the carboxylate, it also depends on the concentration of the lanthanide. It may therefore be more significant to express the amount of water present in the solution as the molar ratio $H_2O/Ln$ and consequently the latter can vary from 0.5 to values of around 1.4-1.5. All these solutions can be easily treated, according to the process of the present invention, until a much lower molar $H_2O/Ln$ ratio than the starting ratio, is obtained at the end of the treatment.

The quantity of residual $H_2O$ in the hydrocarbon solutions of the lanthanide carboxylates, diminishes with the increase of the initial weight ratio between $H_2O$ and solid product used and of the contact time between solid and solution. Consequently, according to a preferred aspect of the present invention, the hydrocarbon solution containing the lanthanide carboxylate is circulated in continuous, by using a suitable pump, through a column having appropriate dimensions, filled with one of the solid products described in step b). Molecular sieves 3 Å, molecular sieves 4 Å or a mixture thereof are preferably used, even more preferably molecular sieves 3 Å are adopted.

Steps a) and/or b) of the process of the present invention can be repeated several times to obtain the desired purity degree of the lanthanide carboxylate solution as far as the water and/or carboxylic acid content is concerned.

With the method of the present invention, it is possible to obtain hydrocarbon solutions of lanthanide carboxylate wherein the molar ratios between lanthanide and protogenic substances, such as water and carboxylic acid, are in the range of detection limit of normal analytical techniques, typically: $Ln/H_2O > 60$ and $Ln/RCOOH > 100$. The solutions obtained according to the process of the present invention can be used as such for subsequent polymerization processes without requiring the high vacuum solvent evaporation steps as described in the prior documents. Furthermore, it has been found that, unexpectedly with respect to what is described in U.S. Pat. No. 6,111,082, the cyclohexane solutions of lanthanide carboxylate, in particular neodymium versatate, obtained through the purification process of the present invention, wherein water and acid are practically absent, have proved to be indefinitely stable with time and, in practice, also after several weeks no precipitation of product is observed. The stable cyclohexane solutions thus obtained, characterized by $Ln/H_2O > 60$ and $Ln/RCOOH > 100$, represent a further object of the present invention and are directly used in the polymerization of conjugated dienes, for example isoprene or butadiene, preferably butadiene, giving better performances in terms of molecular weight, which is lower, and reaction kinetics which are faster.

The purification methods described above can be used for any lanthanide carboxylate solution containing carboxylic acid and/or water, regardless of the synthesis method used. According to the method of the present invention, cyclohexane solutions of $Nd(Vers)_3$ can be treated, obtained by reaction of $Nd_2O_3$ and versatic acid, as described, for example, in U.S. Pat. No. 5,686,371 EP 0,562,081 or EP 0,968,992. Similarly, cyclohexane solutions of $Nd(Vers)_3$ can be treated, obtained by the reaction of $NdCl_3$ with $Na(Vers)$, as described, for example, in U.S. Pat. No. 4,520,177 or U.S. Pat. No. 6,111,082. The possibility of having solutions of lanthanide carboxylates with a water and/or versatic acid content which can be regulated, using the method of the present invention, until product samples are obtained practically free of water and carboxylic acid, also allows, if necessary, the preparation, by a simple evaporation of the solvent at reduced pressure, using normal equipment well-known to the experts in the field, of lanthanide solid carboxylates having a purity degree corresponding to that of the starting solution.

The achievement of the desired purity degree can be followed and controlled by means of new analysis methods based on the use of suitable and particular parameters of IR spectroscopy or spectroscopy in the visible region.

In particular, new methods allow the quantity of carboxylic acid and/or water directly present in the solutions containing lanthanide carboxylates to be measured, after suitable calibrations, in a non-destructive manner.

With reference to IR spectroscopy, it has in fact been found that in the IR spectra and more specifically in the region between 1800 and 1475 $cm^{-1}$, the addition of progressive amounts of carboxylic acid to reference hydrocarbon solutions of the corresponding pure lanthanide carboxylate, causes a decrease in the intensity of the band at 1514 $cm^{-1}$, which is characteristic of lanthanide carboxylate and corresponding to the carboxylate ligand which is bridge-bounded to three lanthanide centres, and the parallel increase of an absorption band at 1560 $cm^{-1}$, together with two bands at 1663 and 1700 $cm^{-1}$.

The band at 1560 $cm^{-1}$ was attributed to the carboxylate ligand bridge-bounded between two lanthanide centres, whereas the two bands at 1663 and 1700 $cm^{-1}$ were attributed to the carboxylic acid coordinated to a single lanthanide center and to the free carboxylic acid in excess, respectively.

The areas of the absorbing bands centred at 1700 and 1663 $cm^{-1}$, for each of the reference solutions, divided by the concentration of the lanthanide present in each of the reference solutions, is indicated in a graph with respect to the corresponding carboxylic acid/lanthanide molar ratio: the curve thus obtained allows the calculation of the carboxylic acid content of any solution deriving from the synthesis of the corresponding lanthanide carboxylate, containing the carboxylate and said acid as impurity.

It has been found that the addition of water to hydrocarbon solutions of the corresponding pure lanthanide carboxylate, causes, in the IR spectra, a decrease in the intensity of the 1514 $cm^{-1}$ band, characteristic of lanthanide carboxylate and corresponding to the carboxylate ligand which is bridge-bounded with three lanthanide centres, and the parallel increase of an absorption band at 1560 $cm^{-1}$, together with a band at 1685 $cm^{-1}$. The band at 1560 $cm^{-1}$ was attributed to the carboxylate ligand which is bridge-bounded between two lanthanide centres, whereas the 1685 $cm^{-1}$ band was attributed to the carboxylate reversibly protonated by water, with the formation of carboxylic acid coordinated to neodymium.

The area of the absorption band centred at 1685 $cm^{-1}$, for each of the reference solutions, divided by the molar concentration of the lanthanide present in the solution, is shown in a graph with respect to the corresponding $H_2O$/lanthanide molar ratio. The curve allows the calculation of the water content of any solution deriving from the synthesis of a lanthanide carboxylate containing water as impurity.

In accordance with the above, an object of the present invention relates to a method for determining the content of carboxylic acid and/or water of a solution of the corresponding lanthanide carboxylate, containing said acid and/or water as impurities, which comprises the following steps:

1) measuring the molar concentration of lanthanide in the solution [Ln]

2) recording the IR spectrum of the solution and calculating the IA/[Ln] ratio, by dividing the area corresponding to the absorption within the range 1750-1600 cm$^{-1}$ (IA), resolved before in the relative water and acid bands, if both are present, by the molar concentration of lanthanide, 3) obtaining, for the value or the values obtained in the previous item 2) the corresponding value of the carboxylic acid/lanthanide and/or water/lanthanide molar ratio making use of the relative calibration curve constructed by indicating, in the abscissa, the different carboxylic acid/lanthanide or water/lanthanide molar ratios of reference solutions containing known amounts of carboxylic acid and lanthanide or water and lanthanide, and, in the ordinate, the values of the ratio IA/[Ln] corresponding to those reference solutions, wherein IA is the area of the absorbing IR bands within the range of 1750-1600 cm$^{-1}$ for each reference solution, recorded under the same conditions as step 2), and [Ln] is the relative lanthanide concentration.

According to a preferred aspect of the present invention, it is therefore possible, in particular, to determine the content of carboxylic acid of a solution of the corresponding lanthanide carboxylate containing said acid as impurity, by means of a method comprising the following steps:

1) measuring the molar concentration of lanthanide in the solution [Ln]

2) recording the IR spectrum of the solution and calculating the IA/[Ln] ratio, by dividing the area of the absorption bands centred at 1700 and 1663 cm$^{-1}$ (IA) by the molar concentration of lanthanide, 3) obtaining, for the value obtained in the previous item 2), the corresponding value of the carboxylic acid/lanthanide molar ratio, which can be converted into the relative moles of carboxylic acid by multiplying by [Ln], with the use of a calibration curve constructed by indicating, in the abscissa, the different carboxylic acid/lanthanide molar ratios of reference solutions containing known amounts of carboxylic acid and lanthanide, and, in the ordinate, the values of the ratio IA/[Ln] corresponding to those reference solutions, wherein IA is the area of the absorbing IR bands centred at 1700 and 1663 cm$^{-1}$ for each reference solution, recorded under the same conditions as step 2), and [Ln] is the relative lanthanide concentration.

The preparation of the reference solutions of lanthanide carboxylate containing different and controlled amounts of carboxylic acid as impurity, can be effected by means of any known method.

The same conditions, in particular the same cell at a known depth, must be used for recording the IR spectrum in step 2) and the IR spectra for preparing the calibration curve in step 3).

Figure 2A:
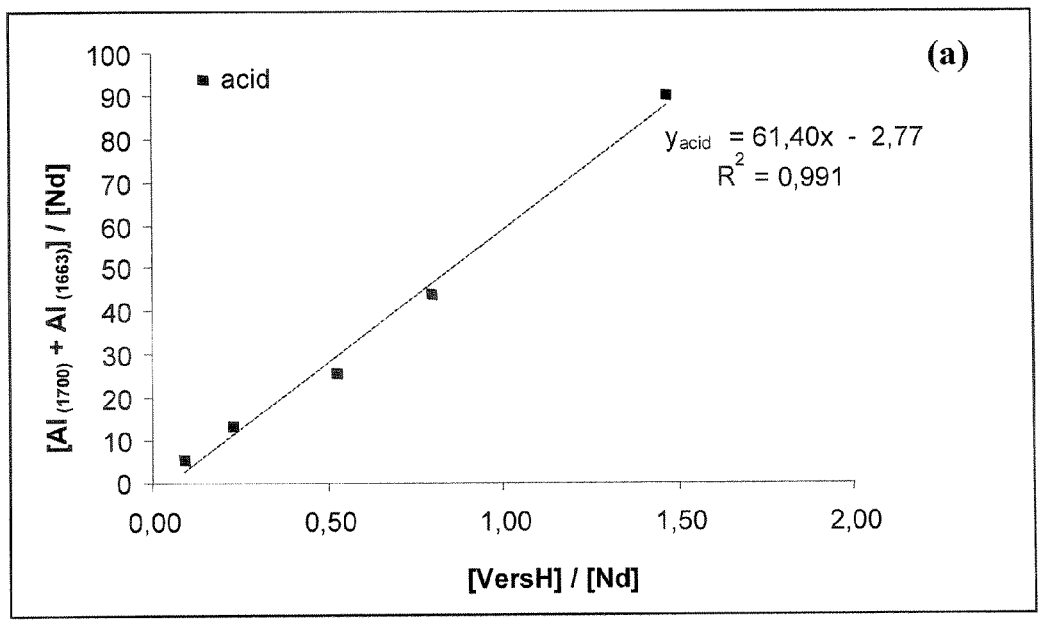
FIG. 2a. A calibration curve for determining by means of IR spectroscopy the content of versatic acid in a solution of $Nd(Vers)_3$.

The method described above is preferably used for solutions containing neodymium carboxylate as lanthanide carboxylate. For a better understanding of what is described above, FIG. 1 shows, in particular, the IR spectrum of a cyclohexanic solution of pure Nd(Vers)$_3$ (dotted line) and the IR spectrum obtained after the addition, to the same solution, of versatic acid (broken line, Nd(Vers)$_3$/VersH molar ratio 1:1.47), whereas FIG. 2a shows a calibration curve for determining, by IR spectroscopy, the content of versatic acid in a solution of Nd(Vers)$_3$, whose construction is described in the examples appearing in the experimental part of the present patent application.

According to another preferred aspect of the present invention, it is possible, in particular, to determine the content of water of a solution containing a lanthanide carboxylate and water as impurity, by means of a method which includes the following steps:

1) measuring the molar concentration of lanthanide in the solution [Ln]

2) recording the IR spectrum of the solution and calculating the IA/[Ln] ratio by dividing the area of the absorption band centred at 1685 cm$^{-1}$ (IA) by the molar concentration of lanthanide, 3) obtaining, for the value obtained in the previous item 2), the corresponding value of the water/lanthanide molar ratio, which can be converted into the relative moles of water, by multiplying by [Ln], with the use of a calibration curve constructed by indicating, in the abscissa, the different water/lanthanide molar ratios of reference solutions containing known amounts of water and lanthanide, and, in the ordinate, the values of the IA/[Ln] ratio corresponding to those reference solutions, wherein IA is the area of the absorbing IR band centred at 1685 cm$^{-1}$ for each reference solution, recorded under the same conditions as step 2), and [Ln] is the relative lanthanide concentration.

The preparation of reference solutions of lanthanide carboxylate containing different and controlled amounts of water as impurity, can be effected using any known method.

The same conditions, in particular the same cell at a known depth, must be used for recording the IR spectrum in step 2) and the IR spectra for preparing the calibration curve in step 3).

The method described above for measuring the water content, is preferably used for solutions containing neodymium carboxylate. For a better understanding of what is described above, FIG. 1 shows, in addition to the IR spectrum of a cyclohexanic solution of pure Nd(Vers)$_3$ (dotted line), the IR spectrum obtained after the addition of water, to the same solution, (continuous line, Nd(Vers)$_3$/H$_2$O molar ratio 1:1.5), whereas FIG. 2a shows a calibration curve for determining, by IR spectroscopy, the content of water in a solution of Nd(Vers)$_3$, whose construction is described in the examples of the present patent application.

It is possible to obtain the profile of the spectrum within the range 1750-1600 cm$^{-1}$ of lanthanide carboxylate samples containing unknown amounts of carboxylic acid and water, for example neodymium carboxylate, in the various component bands, by means of a simple mathematical "curve-fitting" procedure (effected by means of common software for the elaboration of spectra known to technical experts, such as that described in GRAMS/AI of Thermo Electron Corporation): carboxylic acid and water are clearly calculated from the area of the bands thus obtained, on the basis of the calibration curves previously prepared.

The attainment of the desired purity degree for solutions of lanthanide carboxylates can be also detected and controlled by means of a new analysis method based on the use of particular and suitable spectroscopy parameters in the visible region.

In particular, the method allows, after suitable calibration, the calculation of the amount of carboxylic acid and/or water contained directly in solutions of lanthanide carboxylates, in a non-destructive way: the Applicant has found, in fact, that in the absorption spectra in the visible and near infrared region, in particular in the area of 400 and 950 nm, where normally each lanthanide has the electronic absorption bands, relating to the f-f transitions, the progressive addition of water and/or carboxylic acid to hydrocarbon solutions of the corresponding pure lanthanide carboxylate, cause a considerable increase in intensity of said lanthanide carboxylate bands. The variation in intensity was interpreted as evidence of the different type of coordination of the carboxylate ligands at the center of the lanthanide, caused by the reaction with water and carboxylic acid, i.e. to the variation in the type of coordination of the carboxylate ligand, from bridge-bounded with three lanthanide centres to bridge-bounded between two lanthanide centres or coordinated on a single lanthanide centre. The value of the areas of the bands of the spectrum, in particular the most intense band, therefore provides the measurement of the quantity of acid and/or water present in the lanthanide carboxylate solution.

An object of the present invention therefore relates to a method for determining the content of carboxylic acid and/or water of a solution of the corresponding lanthanide carboxylate containing said acid and/or water as impurities, which comprises the following steps:

1) measuring the molar concentration of lanthanide in the solution [Ln]

2) recording the visible spectrum of the solution and calculating the IA/[Ln] ratio by dividing the area of one of the bands of the lanthanide carboxylate spectrum (IA), preferably the most intense band, by the molar concentration of lanthanide, 3) obtaining, for the value obtained in the previous item 2), the corresponding value of the carboxylic acid/lanthanide and/or water/lanthanide molar ratio, with the use of a calibration curve constructed by indicating, in the abscissa, the different carboxylic acid/lanthanide or water/lanthanide molar ratios of reference solutions containing known amounts of carboxylic acid and lanthanide or water and lanthanide, and, in the ordinate, the values of the IA/[Ln] ratio corresponding to those reference solutions, wherein IA is the area, for each reference solution, of the band which is at the same wave-length as that used in step 2) and which has been recorded under the same conditions as step 2), and [Ln] is the relative lanthanide concentration.

According to a preferred aspect of the present invention, it is possible, in particular, to determine the content of carboxylic acid of a solution of the corresponding lanthanide carboxylate containing said acid as impurity, which comprises the following steps:

1) measuring the molar concentration of lanthanide in the solution [Ln]

2) recording the visible spectrum of the solution and calculating the IA/[Ln] ratio by dividing the area of one of the bands present in the spectrum of lanthanide carboxylate (IA), preferably the most intense band, by the molar concentration of lanthanide, 3) obtaining, for the value obtained in the previous item 2), the corresponding value of the carboxylic acid/lanthanide molar ratio, which can be converted into the relative moles of acid, by multiplying by [Ln], with the use of a calibration curve constructed by indicating, in the abscissa, the different carboxylic acid/lanthanide molar ratios of reference solutions containing known amounts of carboxylic acid and lanthanide, and, in the ordinate, the values of the IA/[Ln] ratio corresponding to those reference solutions, wherein IA is the area of each reference solution, of the band at the same wave-length as that used in step 2), recorded under the same conditions as step 2), and [Ln] is the relative lanthanide concentration.

The preparation of the reference solutions of lanthanide carboxylate containing different and controlled amounts of carboxylic acid as impurity, can be effected by means of any known method.

The same conditions, in particular the same cell at a known depth, must be used for the recording the visible spectrum in step 2) and the visible spectra for preparing the calibration curve in step 3).

In particular, for neodymium the band preferably used for obtaining a measurement of the amount of carboxylic acid in a solution of neodymium carboxylate, is that centred around 584 nm, [assigned to the transition of $^4G_{5/2}(^2G_{7/2}) \leftarrow {}^4I_{9/2}$ according to what is shown in A. Kumar, D. K. Rai and S. B. Rai, Spectrochimica Acta Part A, volume 58 (2002), pages 1379-1387].

Figure 3:
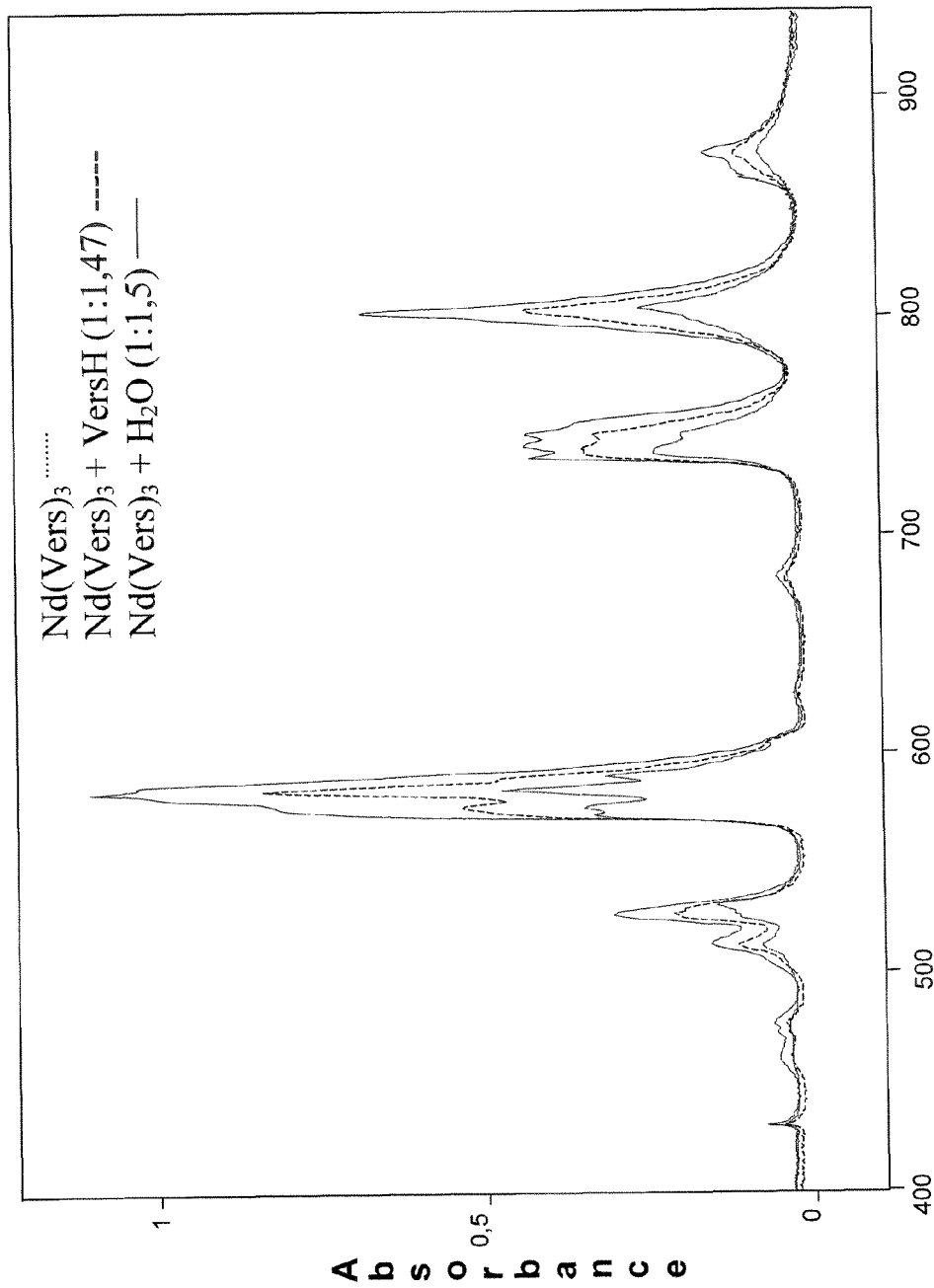
FIG. 3. The spectrum in the visible region of a cyclohexane solution of pure $Nd(Vers)_3$ (dotted line) and the spectrum obtained after the addition of versatic acid (broken line, $Nd(Vers)_3$/VersH molar ratio 1:1.47).

FIG. 3 shows the spectrum in the visible region of a cyclohexane solution of pure $Nd(Vers)_3$ (dotted line) and the spectrum obtained after the addition of versatic acid (broken line, $Nd(Vers)_3$/VersH molar ratio 1:1.47).

Figure 4:
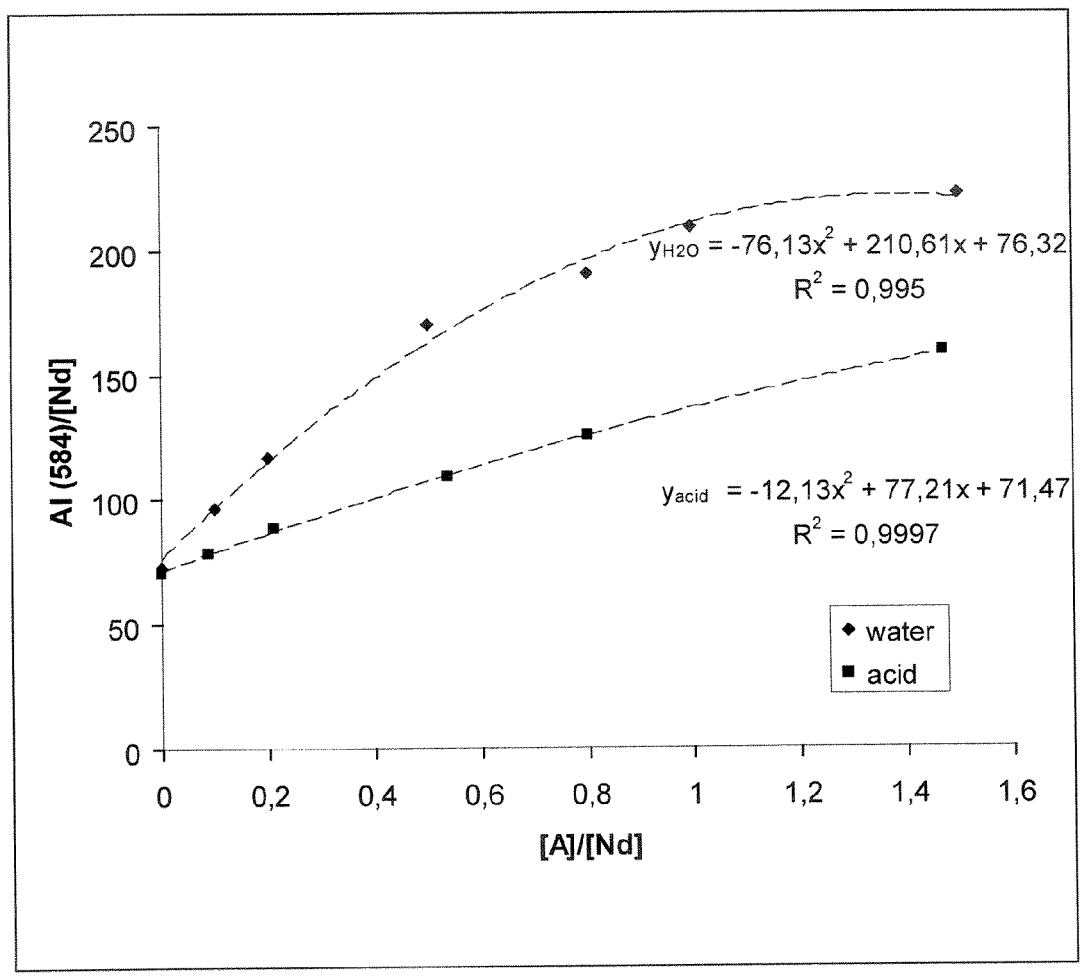
FIG. 4. A calibration curve for determining, through visible spectroscopy, the content of versatic acid in a solution of $Nd(Vers)_3$, whose construction is described in the examples of the present patent application (- -■- -).

FIG. 4 shows a calibration curve for determining, through visible spectroscopy, the content of versatic acid in a solution of $Nd(Vers)_3$, whose construction is described in the examples of the present patent application (- -■- -).

According to another preferred aspect of the present invention, it is possible to determine the water content of a solution of lanthanide carboxylate containing water as impurity, which includes the following steps:

1) measuring the molar concentration of lanthanide in the solution [Ln]

2) recording the visible spectrum of the solution and calculating the IA/[Ln] ratio by dividing the area of one of the bands present in the spectrum of the lanthanide carboxylate (IA) considered, preferably the most intense band, by the molar concentration of lanthanide, 3) obtaining, for the value obtained in the previous point 2) the corresponding molar ratio $H_2O$/lanthanide, using the calibration curve constructed by indicating, in the abscissa, the different water/lanthanide molar ratios of reference solutions containing known quantities of water and lanthanide, and, in the ordinate, the values of the IA/[Ln] ratio corresponding to those reference solutions, wherein IA is the area of each reference solution, of the band at the same wave-length as that used in step 2), recorded under the same conditions as step 2), and [Ln] is the relative lanthanide concentration.

The same conditions, in particular the same cell at a known depth, must be used for recording the visible spectrum in step 2) and the spectra for preparing the calibration curve in step 3).

The preparation of the reference solutions of lanthanide carboxylate containing different and controlled amounts of water as impurity, can be effected by means of any known method.

In particular, also in this case, for neodymium the band preferably used is that centred around 584 nm, [assigned to the transition of $^4G_{5/2}(^2G_{7/2}) \leftarrow {}^4I_{9/2}$ according to what is indicated in A. Kumar, D. K. Rai and S. B. Rai, Spectrochimica Acta Part A, volume 58 (2002), pages 1379-1387].

FIG. 3 shows the spectrum in the visible region of a cyclohexane solution of pure $Nd(Vers)_3$ (dotted line) and the spectrum obtained after the addition of water to the same solution (broken line, $Nd(Vers)_3/H_2O$ molar ratio 1:1.5).

FIG. 4 shows a calibration curve for determining, through visible spectroscopy, the content of water in a solution of $Nd(Vers)_3$, whose construction is described in the examples of the present patent application (- -♦- -).

When water and versatic acid are both present, the upper and lower limit of the sum of relative molar concentrations can be estimated, using the acid curve, whose effect is weaker and the water curve, whose effect is stronger, respectively. When both water and acid are contained in the solutions as impurities, the greater the difference in concentration between water and acid, the more accurate the evaluation of their concentrations will be by means of visible spectroscopy.

A further object of the present invention relates to the purification process of the present invention wherein the initial content of hydrocarbon solution deriving from the synthesis of lanthanide carboxylate in terms of water or carboxylic acid and/or the attainment of the desired purity in terms of water or carboxylic acid content, are followed, controlled and verified by means of one or more of the analytical methods claimed above.

EXAMPLES

The analytical techniques and characterization methods briefly described and listed hereunder were used in the following examples.

The measurements effected by means of IR spectroscopy mentioned in the following examples were carried out by means of a transmission spectrophotometer Nicolet Nexus, using a cell for liquids having an optical path equal to 0.005 cm, equipped with windows of $CaF_2$ and charging the solutions under anhydrous conditions.

The measurements effected by means of visible spectroscopy and mentioned in the following examples, were carried out by means of a Perkin Elmer spectrophotometer (Λ-19 model) using Suprasil quartz cells with an optical path of 1 cm and a screw-stopper or tap to allow the charging and preservation of the sample under anhydrous conditions.

The molecular weight measurements of the polymers was effected by means of Gel-Permeation chromatography (GPC). The analyses of the samples were carried out in tetrahydrofuran (stabilized with Irganox) at 40° C., using a Waters differential refractometer as detector. The chromatographic separation was obtained with a set of PL-MIXED columns, by establishing a flow-rate of the eluent of 1 ml/min. The data were acquired and processed by means of Maxima 820 software version 3.30 (Millipore) and the molecular mass determination was effected according to the universal calibration method (k=0.000212 α=0.739).

The determination of the content of 1,4-cis, 1,4-trans and 1,2-units in the polybutadienes produced was effected by means of the known techniques based on IR spectroscopy.

The commercial reagents listed below were used in the preparations described in the examples:

| | |
|---|---|
| neodymium oxide $Nd_2O_3$ | STREM |
| neodymium carbonate $(Nd_2(CO_3)_3$ | STREM |
| hydrochloric acid HCl (normex) | C.ERBA |
| sodium hydroxide NaOH (normex) | C.ERBA |
| molecular sieves (3 Å) | ALDRICH |
| basic alumina (pellets) | ALDRICH |
| versatic acid | SHELL |
| 1,3 butadiene (99.95%) | RIVOIRA |
| diisobutylaluminum hydride $Al(iso-Bu)_2H$ | DIBAH ALDRICH |
| diisobutylaluminum chloride $Al(iso-Bu)_2Cl$ | DIBAC ALDRICH |

The reagents and/or solvents used and not indicated above are those commonly used in laboratory techniques and on an industrial scale and can be easily found at the premises of commercial operators specialized in the field.

Example 1

Preparation of $Nd(Vers)_3$ from $NdCl_3$ and NaVers a) Preparation of an Aqueous Solution of $NdCl_3$ 4.21 g of $Nd_2O_3$ (25.02 mgA) and 20 ml of $H_2O$ are charged into a 250 ml flask, equipped with magnetic stirring. The mixture is amalgamated by leaving it under light stirring for about 10 min., after which 73.9 ml of HCl (1M) are added, by means of a dosage burette and the whole mixture is kept under stirring at room temperature for 3 h. At the end of this phase, a slightly turbid light-blue coloured aqueous solution is obtained, having a pH=6.9. After being filtered to eliminate traces of non-reacted $Nd_2O_3$, the solution is brought to volume in a 250 ml calibrated flask and used in the preparations described hereunder [Nd]=0.0985 (99.4% yield with respect to HCl).

b) Preparation of an Aqueous Solution of Sodium Versatate (NaVers)

12.7 g of versatic acid (73.7 mmoles) and about 20 ml of $H_2O$ are charged into a 250 ml flask, equipped with a magnetic stirrer, two phases are formed due to the poor solubility of versatic acid in water. 73.9 ml of NaOH (1M) are added, in about 30 minutes, to the mixture maintained under stirring at room temperature, thus obtaining a slightly opalescent aqueous solution having a pH=11.4. The solution is then filtered and brought to volume in a calibrated flask and used in the preparations described hereunder. [Na(Vers)]=0.296 M, calculated by the NaOH equivalents used.

c) Preparation of $Nd(Vers)_3$ 80 ml of an aqueous solution of $NdCl_3$ ([Nd]=0.0985 M, 7.88 mmoles), obtained as described in the previous point (a) and 80 ml of cyclohexane are transferred to a 250 ml flask, equipped with a magnetic stirrer. 79.5 ml of aqueous solution of NaVers (23.5 mmoles), prepared as described under point (b), are added, by means of a drip funnel, to the mixture thus obtained, maintained under stirring at room temperature. At the end of the addition, the mixture is stirred vigorously for a further 10 minutes and then transferred to a separating funnel. After decanting, the underlying aqueous phase is eliminated and the residual organic phase is washed with water (2×50 ml). By operating in this way, 75 ml of a cyclohexane solution of $Nd(Vers)_3$ having [Nd]=0.089 M, are recovered.

Example 2a

Construction of a Calibration Curve for Determining by Means of Visible Spectroscopy the Content of Water or Versatic Acid in a Solution of $Nd(Vers)_3$ The solid $Nd(Vers)_3$ used in this example, was prepared by drying the cyclohexane solution prepared in the previous example 1 and drying the product obtained under high vacuum at 60-80° C. for 18 hours.

The solid sample resulting from this drying treatment has $H_2O/Nd \leqq 0.002$ (molar ratio), obtained with "Karl Fisher" titration and VersH/Nd$\leqq$0.001 (molar ratio), obtained with acid-base titration.

0.3139 g of solid $Nd(Vers)_3$, obtained as described above and 9.225 g of cyclohexane are charged into a tailed Schlenk-tube equipped with a magnetic stirrer. The mixture is left under stirring for 24 hours at room temperature in order to obtain a homogeneous solution with [Nd]=0.042 M. Six equal portions of the solution thus obtained are introduced into the same number of tailed Schlenk-tubes equipped with a magnetic stirrer and to each Schlenk-tube, the appropriate quantity of versatic acid is added, by means of a micro-syringe. The solutions thus prepared have a content of versatic acid, calculated as a molar ratio VersH/Nd, varying from 0 to 1.47, in particular, in the various solutions, the molar ratio VersH/Nd is equal to 0.0-0.10-0.22-0.55-0.80-1.47. After maintaining them under stirring at room temperature for 15 minutes, they are transferred to the specific quartz cells and the spectrum from 500 to 700 nm is registered. The absorption band area centred at 584 nm (AI (584)), divided by the molar concentration of Nd present ([Nd]), is indicated in a graph with respect to the VersH/Nd molar ratio, for the various solutions analyzed. The results obtained are specified in FIG. 4, where [A] refers to [VersH], together with the corresponding calibration curve of the equation $Y_{acid}=-12.13X^2+77.21X+71.47$ (- -■- -).

With a completely analogous procedure to that described above, seven cyclohexane solutions of $Nd(Vers)_3$ are prepared with [Nd]=0.042 M having a $H_2O$ content, calculated as $H_2O$/Nd molar ratio, varying from 0 to 1.5, in particular, in the various solutions, the $H_2O$/Nd molar ratio is equal to 0.0-0.12-0.20-0.50-0.80-1.00-1.50, and the spectrum from 500 to 700 nm is registered. Also in this case, the absorption band area centred at 584 nm, divided by the molar concentration of Nd present, is indicated in a graph with respect to the $H_2O$/Nd molar ratio, for the various solutions analyzed.

The results obtained are specified in FIG. 4, where [A] refers to [$H_2O$], together with the corresponding calibration curve of the equation $Y_{H2O}=-76.13X^2+210.61X+76.32$ (- -◆- -).

The curves indicated in FIG. 4 allow the [A]/[Nd] molar ratio to be determined, by means of visible spectroscopy, wherein A=versatic acid or $H_2O$, in cyclohexane solutions of $Nd(Vers)_3$, by knowing the relative value of the absorption band area centred at 584 nm AI(584) measured under the same conditions used for the construction of the calibration curve.

Example 2b

Construction of a Calibration Curve for Determining by Means of IR Spectroscopy the Content of Water or Versatic Acid in a Solution of $Nd(Vers)_3$ The solid $Nd(Vers)_3$ used in this example, was prepared by drying the cyclohexane solution prepared in the previous example 1 and drying the product obtained under high vacuum at 60-80° C. for 18 hours.

The solid sample resulting from this drying treatment has $H_2O$/Nd≦0.002 (molar ratio), obtained with "Karl Fisher" titration and VersH/Nd≦0.001 (molar ratio), obtained with acid-base titration.

0.3921 g of solid $Nd(Vers)_3$, prepared as described above and 10.837 g of cyclohexane are charged into a tailed Schlenk-tube equipped with a magnetic stirrer. The mixture is left under stirring for 24 hours at room temperature in order to obtain a homogeneous solution with [Nd]=0.044 M. Following the same procedure described in example 1, the solution thus obtained is divided into five equal parts and a known quantity of versatic acid is added to each portion so that the molar ratio VersH/Nd varies from 0.1 to 1.5, in particular, in the various solutions, the molar ratio VersH/Nd is equal to 0.10-0.22-0.55-0.80-1.47. Finally, the spectrum of the various solutions in the area between 1800 and 1450 cm$^{-1}$ is registered. The absorption band area centred at 1700 and 1663 cm$^{-1}$, divided by the molar concentration of Nd present, is subsequently indicated in a graph with respect to the VersH/Nd molar ratio, for the various solutions analyzed. The results obtained are specified in FIG. 2a, together with the corresponding calibration curve of the equation $Y_{acid}=61.40X-2.77$.

With a completely analogous procedure to that described above, six cyclohexane solutions of $Nd(Vers)_3$ are prepared with [Nd]=0.044 M having a $H_2O$ content, calculated as $H_2O$/Nd molar ratio, varying from 0.1 to 1.4, in particular, in the various solutions, the $H_2O$/Nd molar ratio is equal to 0.12-0.25-0.50-0.80-1.00-1.40, and the IR spectrum from 1800 to 1450 cm$^{-1}$ is registered. The area of the absorption band centred at 1685 cm$^{-1}$, divided by the molar concentration of Nd present, is indicated in a graph with respect to the $H_2O$/Nd molar ratio, for the various solutions analyzed.

Figure 2B:
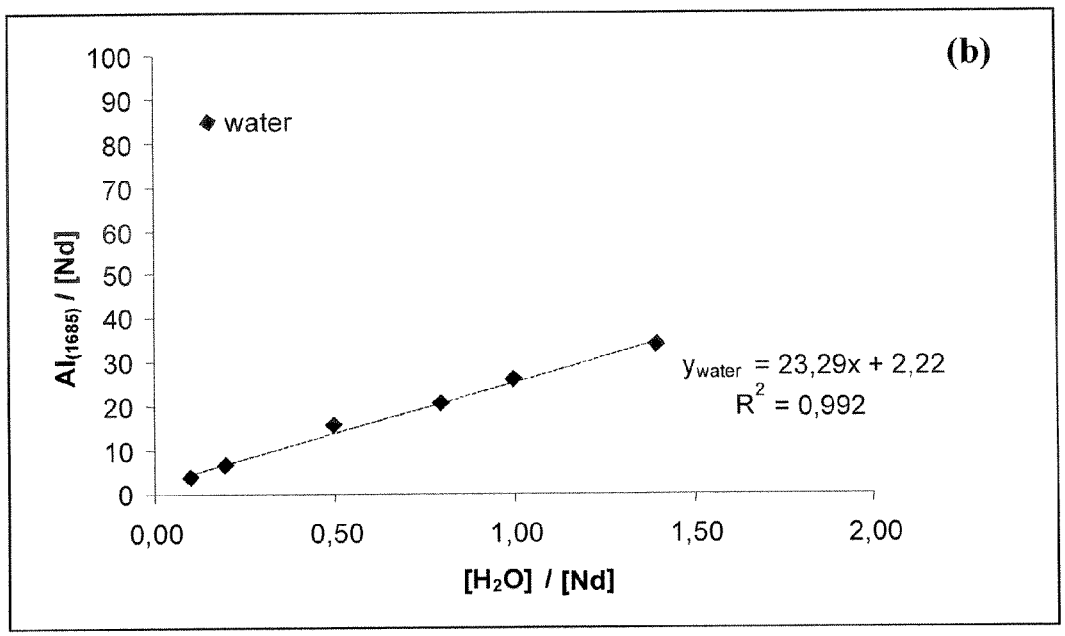
FIG. 2b. A calibration curve for determining by means of IR spectroscopy the content of water in a solution of Nd $(Vers)_3$.

The results obtained are specified in FIG. 2b, together with the corresponding calibration curve of the equation $Y_{H2O}=23.29X+2.22$.

The curves indicated in FIGS. 2a and 2b allow the [A]/[Nd] molar ratio to be determined, by means of IR spectroscopy, wherein A=versatic acid or $H_2O$, in cyclohexane solutions of $Nd(Vers)_3$, once the relative IR absorption has been measured under the same conditions.

Example 3

Preparation of $Nd(Vers)_3$ from $Nd_2O_3$ and Versatic Acid (a) The following products are charged in order into a 250 ml flask, equipped with a magnetic stirrer and a bubble cooler: 7.21 g of $Nd_2O_3$ (42.85 mgA), 29.52 g of versatic acid (171.4 mmoles), 100 ml of cyclohexane and a catalytic quantity of HCl (37%). The reaction mixture is then heated to the reflux temperature of the solvent for about 3 hours. In this phase, all of the solid present in the reaction container almost totally dissolves and a deep blue-purple-coloured solution is obtained, having [Nd]=0.42 M. The IR spectrum between 1880 and 1450 cm$^{-1}$ and the Visible spectrum between 500 and 700 nm of this solution are measured, under the same conditions and with the same equipment as examples 2a and 2b, and the results obtained are indicated on the calibration curves of examples 2a and 2b, providing the following results: VersH/Nd=0.9 (molar ratio); $H_2O$/Nd=1.2 (molar ratio). The versatic acid and water analyses are repeated with the known invasive acid-base titration and "Karl Fisher" titration methods respectively, and the results, substantially confirming those measured with the spectroscopic methods of the present invention, are as follows: VersH/Nd=0.9 (molar ratio); $H_2O$/Nd=1.3 (molar ratio).

(b) A part of the solution previously obtained, is treated, under vigorous stirring, with a solution of NaOH (0.1 M) until the pH value of the aqueous phase is stably maintained at 11.5. After 2 hours, the phases are separated, the organic phase is washed with two 20 ml fractions of $H_2O$ and 40 ml of a cyclohexane solution of $Nd(Vers)_3$ are obtained, having [Nd]=0.41 M: the IR spectrum between 1880 and 1450 cm$^{-1}$ and the Visible spectrum between 500 and 700 nm of this solution are measured, under the same conditions and with the same equipment as examples 2a and 2b, and the results obtained are indicated on the calibration curves of examples 2a and 2b, providing the following results: VersH/Nd=0.012 (molar ratio); $H_2O$/Nd=1.3 (molar ratio).

Example 4

Preparation of $Nd(Vers)_3$ from $Nd_2(CO_3)_3$ and Versatic Acid

The following products are charged in order into a 250 ml flask, equipped with a magnetic stirrer and a bubble cooler: 8.15 g of $Nd_2(CO_3)_3$ (34.79 mgA), 22.16 g of versatic acid (128.7 mmoles), 100 ml of cyclohexane and a catalytic quantity of HCl (37%). Operating as described above in example 3, a blue-purple-coloured cyclohexane solution is obtained, which is accompanied, in this case, by a vigorous development of gas. The reaction mixture is then cooled to room temperature and, a solution of NaOH (1 M) is added, under vigorous stirring, until the pH value of the aqueous phase is stably maintained at 10.5. After 2 hours, the phases are separated, the organic phase is washed with two 20 ml fractions of $H_2O$ and 95 ml of a cyclohexane solution of $Nd(Vers)_3$ are obtained, which is put in contact with molecular sieves (3 Å) for 24 hours. After this treatment, the IR spectrum between 1880 and 1450 $cm^{-1}$ and the Visible spectrum between 500 and 700 nm of the solution, having [Nd]=0.33 M, are measured, under the same conditions and with the same equipment as examples 2a and 2b, and the results obtained are indicated on the calibration curves of examples 2a and 2b, providing the following results: VersH/Nd=0.5 (molar ratio); $H_2O$/Nd=0.03 (molar ratio).

Example 5

A cyclohexane solution of $Nd(Vers)_3$, having [Nd]=0.089 M, is obtained by the preparation of example 1.

The IR spectrum between 1880 and 1450 $cm^{-1}$ and the Visible spectrum between 500 and 700 nm of this solution, are measured, under the same conditions and with the same equipment as examples 2a and 2b, and the results obtained are indicated on the calibration curves of examples 2a and 2b, providing the following results: VersH/Nd=0.011 (molar ratio); $H_2O$/Nd=1.4 (molar ratio).

Example 6

Preparation of Anhydrous $Nd(Vers)_3$ (a) 30 ml of the solution of example 5 are transferred to a tailed Schlenk-tube containing an appropriate quantity of molecular sieves 3 Å. After maintaining the solution under these conditions, at room temperature for 36 hours, the IR spectrum between 1880 and 1450 $cm^{-1}$ and the Visible spectrum between 500 and 700 nm, are measured, under the same conditions and with the same equipment as examples 2a and 2b, and the results obtained are indicated on the calibration curves of examples 2a and 2b, providing the following results: $H_2O$/Nd=0.025 (molar ratio).

The process of the present invention allows a solution of lanthanide carboxylate to be obtained in a simple way, which can be used as such in the polymerization of dienes, without having to subject it to vacuum distillation, until the carboxylate is obtained in solid form, to eliminate the acid and water impurities.

(b) Alternatively, in order to speed up the operation of the previous point (a), the solution can be circulated, with a specific pump, through a cartridge suitably filled with molecular sieves 3 Å. In this way, after 2 hours there is a molar ratio of $H_2O$/Nd=0.045, again measured using the calibration curves of examples 2a and 2b.

Examples 7 to 12

Polymerization of Butadiene

Examples 7 to 12 relate to a series of polymerization tests for the preparation of polybutadiene with a high content of 1,4-cis-units, effected using a catalytic system comprising $Nd(Vers)_3$ prepared according to examples 3, 4 and 6, di-iso-butylaluminum hydride DIBAH and di-iso-butylaluminum chloride DIBAC as cocatalysts.

The specific polymerization conditions of each example and the results obtained are indicated in table (I) below, which specifies, in succession, the reference example number; the $Nd(Vers)_3$ used and the example number in which the preparation is described, the content of versatic acid expressed as a molar ratio with respect to the neodymium, the $H_2O$ content expressed as a molar ratio with respect to the neodymium, the temperature increase of the reaction mixture observed by operating under adiabatic conditions, the time used for reaching the maximum temperature, the butadiene conversion and the time used, the number average molecular weight ($M_n$) and the molecular weight value at the peak of the molecular weight distribution curve of the polymer produced ($M_p$).

The polymerization is effected in a 1 liter glass reactor, equipped with a magnetic entrainment anchor stirrer and external jacket connected to a heat exchanger for the temperature control. Before each test, the reactor is previously flushed by washings with anhydrous cyclohexane (2×400 g) at a temperature of 90° C. for at least 2 hours. After discharging the washing solvent, the reactor is cooled to 25° C. and the following products are charged in order: 400 g of anhydrous cyclohexane, the established quantity of di-iso-butylaluminum hydride and di-iso-butylaluminum chloride, as 0.8 M and 0.9 M solutions in cyclohexane, respectively, and 42 g of freshly distilled 1,3-butadiene, by passage from two 1 m steel columns filled with alumina pellets and molecular sieves (3 Å), respectively. The reactor is then brought to the desired polymerization temperature (60° C.) and the cyclohexane solution containing the desired quantity of $Nd(Vers)_3$ is transferred, under a stream of inert gas, to a metallic container, from which it is introduced into the reactor by means of an overpressure of nitrogen.

The polymerization reaction is carried out adiabaticcally, by emptying the reactor jacket as soon as the polymerization reaction has been triggered. After the period of time established (generally varying from 30 to 60 minutes), the polymerization reaction is interrupted by discharging the contents of the reactor, through a valve situated on the bottom, into a suitable container, containing 800 ml of a 2% by weight solution of Irganox in ethyl alcohol. The polymer which is separated is left immersed in this solution for 2 hours, it is then recovered and vacuum dried at a reduced pressure of 1000 Pa, for at least 8 hours, in order to completely eliminate possible traces of non-reacted monomer and solvent. The solid thus obtained is weighed and the conversion calculated, finally the content of 1,4-cis units is measured by means of the known techniques based on IR spectroscopy and the ($M_n$) and ($M_p$) values are calculated by means of GPC analysis. The results obtained are indicated in table I below.

TABLE I polymerization of butadiene according to examples 7 to 12[a].

| Ex. | Nd(Vers)$_3$ (ref.ex.) | VersH/Nd (mol/mol) | H$_2$O/Nd (mol/mol) | ΔT (°C.) | t (T$_{max}$) (min) | Conv. (%) t, (min) | M$_n$ (×10$^{-3}$) | M$_p$ (×10$^{-3}$) |
|---|---|---|---|---|---|---|---|---|
| 7 | 3(a) | 0.9 | 1.2 | — | — | — | — | — |
| 8 | 3(b) | 0.012 | 1.3 | 27 | 15 | 98 in 45' | 149 | 202 |
| 9 | 4 | 0.5 | 0.03 | 29 | 13 | 99 in 45' | 156 | 289 |
| 10 | 6(a) | 0.011 | 0.025 | 34 | 9 | 99 in 30' | 123 | 176 |
| 11 | 6(b) | 0.011 | 0.045 | 31 | 10 | 99 in 35' | 127 | 187 |
| 12[b] | 3(a) | 0.9 | 1.2 | 24 | 20 | 98 in 60' | 120 | 181 |

[a]Each example was carried out using: cyclohexane (400 g), butadiene (42 g), Nd(Vers)$_3$ (0.1 mmoles), DIBAH (0.6 mmoles), DIBAC (0.3 mmoles), by triggering the reaction at 60° C. and effecting the polymerization under adiabatic conditions. All the polybutadienes obtained have a content of 1,4-cis units >96.5%
[b]In this example DIBAH = 1.2 mmoles As it can be seen from the data summarized in Table I, the use of Nd(Vers)$_3$ containing the lowest quantity of versatic acid and water (Ex. 10), allows polybutadiene to be obtained with the lowest molecular weight (M$_n$ and M$_p$). Furthermore, the low versatic acid and water values enable a more rapid reaction kinetics to be obtained (Ex. 10 and 11), as demonstrated by higher ΔT values and by the fact that complete conversions are reached in much shorter times. The presence of greater quantities of water (Ex. 8) or versatic acid (Ex. 9) causes an increase in the molecular weights of the polybutadiene obtained and a significant slowing down of the reaction rate. Finally, the use of Nd(Vers)$_3$ containing high quantities of versatic acid and water (Ex. 7) does not allow a polymer to be obtained, under these conditions. Using the same precursor, it is possible to obtain the polymer by increasing the quantity of DIBAH in the formulation of the catalytic system (Ex. 12). In this case, in fact, by doubling the initial quantity of DIBAH, a polymer is obtained with molecular weights (M$_n$ and M$_p$) comparable to those obtained in example 10, but the polymerization kinetics are much slower: lower ΔT and complete conversion reached in double the time.

The invention claimed is:

1. A process for purifying a hydrocarbon solution deriving from the synthesis of a lanthanide carboxylate, comprising said lanthanide carboxylate and impurities of the corresponding carboxylic acid and/or water, comprising:
treating the hydrocarbon solution, comprising lanthanide carboxylate, with an aqueous solution of a base to obtain a pH of the aqueous phase ranging from 11.0 to 11.8; and
optionally treating the hydrocarbon solution comprising lanthanide carboxylate with a solid selected from the group consisting of Na$_2$SO$_4$, MgSO$_4$, Mg(ClO$_4$)$_2$, molecular sieves 3 Å, molecular sieves 4 Å, molecular sieves 5 Å and molecular sieves 13 X.

2. The process according to claim 1, comprising:
treating the hydrocarbon solution, comprising lanthanide carboxylate, with an aqueous solution of a base to obtain a second hydrocarbon solution with a pH of the aqueous phase ranging from 11.0 to 11.8; and
treating the second hydrocarbon solution comprising lanthanide carboxylate with a solid selected from the group consisting of Na$_2$SO$_4$, MgSO$_4$, Mg(ClO$_4$)$_2$, molecular sieves 3 Å, molecular sieves 4 Å, molecular sieves 5 Å and molecular sieves 13 X.

3. The process according to claim 1, wherein the solution of the base has a concentration ranging from 0.01 to 2 M.

4. The process according to claim 1, wherein the carboxylic acid is a mono-carboxylic acid or polycarboxylic acid comprising from 2 to 40 carbon atoms selected from the group consisting of aliphatic acid, cyclo-aliphatic acid, alicyclic acid and aromatic acid.

5. The process according to claim 4, wherein the acid comprises from 6 to 20 carbon atoms.

6. The process according to claim 5, wherein the acid comprises from 8 to 12 carbon atoms.

7. The process according to claim 6, wherein the acid is versatic acid, naphthenic acid or 2-ethyl hexanoic acid.

8. The process according to claim 1, wherein the solution of lanthanide carboxylate is a solution of neodymium, praseodymium, gadolinium, lanthanum carboxylate, or mixtures thereof.

9. The process according to claim 1, wherein the lanthanide carboxylate is selected from the group consisting of neodymium versatate, neodymium naphthenate and neodymium 2-ethyl-hexanoate.

10. The process according to claim 1, wherein the base is selected from the group consisting of a hydroxide of an alkaline earth metal, an oxide of alkaline earth metal, a hydroxide of alkaline earth metal, an oxide of alkaline earth metal, ammonia and an organic amine.

11. The process according to claim 10, wherein the base is sodium hydroxide or potassium hydroxide.

12. The process according to claim 2, wherein the solid comprises molecular sieves 3 Å.

13. The process according to claim 2, wherein in said treating the hydrocarbon solution comprising lanthanide carboxylate with a solid, the hydrocarbon solution is circulated in continuous, with a pump, through a column filled with a solid selected from the group consisting of Na$_2$SO$_4$, MgSO$_4$, Mg(ClO$_4$)$_2$, molecular sieves 3 Å, molecular sieves 4 Å, molecular sieves 5 Å and molecular sieves 13X.

14. The process according to claim 1, wherein said treating the hydrocarbon solution comprising lanthanide carboxylate with the aqueous solution of a base is repeated.

15. The process according to claim 2, wherein said treating the hydrocarbon solution comprising lanthanide carboxylate with the aqueous solution of a base is repeated.

16. The process according to claim 2, wherein said treating the hydrocarbon solution comprising lanthanide carboxylate with the solid is repeated.

17. The process according to claim 2, wherein said treating the hydrocarbon solution comprising lanthanide carboxylate with the aqueous solution of a base is repeated, and said treating the hydrocarbon solution comprising lanthanide carboxylate with the solid is repeated.

18. The process according to claim 1, wherein the purified hydrocarbon solution has a molar ratio of lanthanide to carboxylic acid of greater than 100.

19. The process according to claim 2, wherein the purified hydrocarbon solution has a molar ratio of lanthanide to carboxylic acid of greater than 100.

20. The process according to claim 2, wherein the purified hydrocarbon solution has a molar ratio of lanthanide to water of greater than 60.

21. The process according to claim 2, wherein the purified hydrocarbon solution has a molar ratio of lanthanide to carboxylic acid of greater than 100, and wherein the purified hydrocarbon solution has a molar ratio of lanthanide to water of greater than 60.

* * * * *

UNITED STATES PATENT AND TRADEMARK OFFICE
CERTIFICATE OF CORRECTION

| | | |
|---|---|---|
| PATENT NO. | : 8,188,304 B2 | Page 1 of 1 |
| APPLICATION NO. | : 11/689719 | |
| DATED | : May 29, 2012 | |
| INVENTOR(S) | : Paolo Biagini et al. | |

It is certified that error appears in the above-identified patent and that said Letters Patent is hereby corrected as shown below:

On the title page, Item (75), the fifth inventor's information is incorrect. Item (75) should read:

-- (75) Inventors: Paolo Biagini, Trecate (IT); Mario Salvalaggio, Moriondo Torinese (IT); Franco Cambisi, Oleggio (IT); Lucia Bonoldi, Milano (IT); Liliana Gila, Casalino (IT) --

Signed and Sealed this
Seventeenth Day of July, 2012

David J. Kappos
*Director of the United States Patent and Trademark Office*